(12) United States Patent
Hashimoto et al.

(10) Patent No.: US 10,932,874 B2
(45) Date of Patent: Mar. 2, 2021

(54) REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 351 days.

(21) Appl. No.: 15/755,141

(22) PCT Filed: May 27, 2016

(86) PCT No.: PCT/JP2016/002577
§ 371 (c)(1),
(2) Date: Feb. 26, 2018

(87) PCT Pub. No.: WO2017/033353
PCT Pub. Date: Mar. 2, 2017

(65) Prior Publication Data
US 2018/0243899 A1    Aug. 30, 2018

(30) Foreign Application Priority Data
Aug. 25, 2015 (JP) ............................. JP2015-165479

(51) Int. Cl.
*B25J 3/00* (2006.01)
*B25J 9/16* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/37; A61B 34/32; A61B 34/35; A61B 34/70; B25J 9/0087; B25J 9/0081;
(Continued)

(56) References Cited

U.S. PATENT DOCUMENTS 4,056,763 A * 11/1977 Debrie ....................... B25J 3/04
   318/675
7,819,859 B2 * 10/2010 Prisco .................... B25J 9/1638
   345/156
(Continued)

FOREIGN PATENT DOCUMENTS

| CN | 1200691 A | 12/1998 |
| CN | 1067776 C | 6/2001 |

(Continued)

OTHER PUBLICATIONS

Apr. 26, 2019 Extended Search Report issued in European Patent Application No. 16838705.8.
(Continued)

*Primary Examiner* — Jason Holloway
(74) *Attorney, Agent, or Firm* — Oliff PLC

(57) ABSTRACT

A remote control robot system includes a master arm, and a slave arm having a plurality of control modes of an automatic mode in which the slave arm operates based on a prestored task program and a manual mode in which the slave arm operates based on manipulation of an operator received by the master arm. The master arm includes one or more motors configured to drive joints of the master arm, and a motor actuator configured to generate a torque instruction value that operates the joints according to an external force applied to the master arm and gives drive current corresponding to the torque instruction value to the motor. The motor actuator generates, when the control mode is the manual mode, the torque instruction value so that the joints
(Continued)

operate according to the external force while resisting a frictional force of the motor.

7 Claims, 4 Drawing Sheets

(51) Int. Cl.
| | |
|---|---|
| A61B 34/37 | (2016.01) |
| G05B 19/418 | (2006.01) |
| B25J 9/00 | (2006.01) |
| B23P 19/04 | (2006.01) |
| B25J 13/00 | (2006.01) |
| B25J 19/04 | (2006.01) |
| B25J 13/08 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 3/00; B25J 9/1669; B25J 13/06; B25J 13/088; B25J 18/00; B25J 9/161; B25J 9/1664; B25J 9/1682; B25J 9/1689; B25J 19/023; B25J 3/04; B25J 9/1633; B25J 9/1628; B25J 13/02; B25J 9/163; B25J 11/008; B25J 13/003; B25J 13/065; B25J 13/025; B25J 13/084; B25J 13/00; B25J 19/04; B25J 9/126; B25J 19/02; B25J 19/06; B25J 11/005; B25J 9/1661; B25J 9/1692; G05B 19/4182; G05B 2219/37297; G05B 2219/39102; G05B 2219/40143; G05B 2219/39004; G05B 2219/40182; G05B 2219/40145; G05B 2219/40387; G05B 2219/40139; G05B 2219/40161; G05B 2219/40146; G05B 2219/40627; G05B 2219/39439; G05B 2219/40022; G05B 2219/39531; G05B 2219/40163; G05B 2219/39533; G05B 2219/35464; G05B 2219/40142; G05B 2219/33007; G05B 2219/40169; G05B 2219/40183; G05B 2219/40134; G05B 2219/40195; G05B 2219/40162; G05B 2219/40136; G06T 7/62; G06T 7/70; B23Q 15/12; H04N 5/23219; H04N 7/181; B23P 19/04; B23P 21/002; B23P 21/00; G06F 3/017; Y10S 901/09; Y10S 901/47; Y10S 901/08; Y10S 901/03; Y10S 901/27; Y10S 901/41; Y10S 901/10; Y10S 901/46; Y10S 901/02

See application file for complete search history.

(56) References Cited

U.S. PATENT DOCUMENTS

| | | | | |
|---|---|---|---|---|
| 9,423,782 | B2* | 8/2016 | Imada | G05B 19/19 |
| 2006/0071625 | A1* | 4/2006 | Nakata | G05B 19/4061 |
| | | | | 318/568.12 |
| 2008/0014051 | A1* | 1/2008 | Garrec | B25J 3/04 |
| | | | | 414/5 |
| 2011/0009880 | A1* | 1/2011 | Prisco | A61B 34/37 |
| | | | | 606/130 |
| 2011/0166706 | A1* | 7/2011 | Prisco | A61B 34/70 |
| | | | | 700/254 |
| 2012/0029529 | A1* | 2/2012 | Jun | A61B 34/76 |
| | | | | 606/130 |

(56) References Cited

U.S. PATENT DOCUMENTS

| | | | | |
|---|---|---|---|---|
| 2013/0224710 | A1* | 8/2013 | Yang | A61B 34/30 |
| | | | | 434/262 |
| 2014/0156074 | A1* | 6/2014 | Seo | B25J 3/04 |
| | | | | 700/257 |
| 2019/0358817 | A1* | 11/2019 | Ghazaei Ardakani | |
| | | | | B25J 13/085 |

FOREIGN PATENT DOCUMENTS

| | | |
|---|---|---|
| JP | S62-49403 A | 3/1987 |
| JP | S63-283878 A | 11/1988 |
| JP | H02-104987 U | 8/1990 |
| JP | H07-276266 A | 10/1995 |
| JP | H11-198067 A | 7/1999 |
| JP | 2003-311661 A | 11/2003 |
| JP | 2007-61924 A | 3/2007 |

OTHER PUBLICATIONS

Hayati S. et al., "Design and Implementation of a Robot Control System With Traded and Shared Control Capability", Proceedings of the International Conference on Robotics and Automation, vol. 3, pp. 1310-1315, 1989.
Aug. 23, 2016 International Search Report issued in International Patent Application No. PCT/JP2016/002577.
Aug. 23, 2016 Written Opinion issued in International Patent Application No. PCT/JP2016/002577.
Feb. 18, 2017 Office Action issued in Taiwanese Patent Application No. 105126753.

\* cited by examiner

REMOTE CONTROL ROBOT SYSTEM

TECHNICAL FIELD

The present disclosure relates to a remote control robot system provided with a master arm and a slave arm.

BACKGROUND ART

Conventionally, remote control robot systems provided with a master arm and a slave arm which operates according to manipulation of the master arm are known. In such a remote control robot system, a system provided with a force assist mechanism of the master arm is known. Patent Document 1 discloses this kind of technology.

Patent Document 1 describes that an electric motor is provided to each joint of the master arm, and the electric motors generate forces so that the mass and inertia force of the master arm are compensated. Here, manipulating inputs of the operator to the master arm are detected by a 6-axis force sensor, input manipulating forces are calculated based on the manipulating inputs, torque instruction values are generated so that the input manipulating forces are reduced, and current corresponding to the torque instruction values is supplied to the electric motors.

REFERENCE DOCUMENT OF CONVENTIONAL ART

Patent Document

[Patent Document 1] JP1999-198067A

DESCRIPTION OF THE DISCLOSURE

Problems to be Solved by the Disclosure

Although the technology described in Patent Document 1 compensates the mass and the inertia force of the master arm, compensation of a frictional force of the motor which drives each joint of the master arm, and a power-train mechanism which transmits the motor output to the joint is not taken into consideration.

SUMMARY OF THE DISCLOSURE

Meanwhile, the present inventors have considered an implementation of a remote control robot system which uses a master arm, and a slave arm having a plurality of control modes of an automatic mode in which it operates based on a prestored task program, a manual mode in which it operates based on the manipulation of an operator received by the master arm, a correctable automatic mode in which it operates based on the task program while being sequentially corrected by the manipulation of the operator received by the master arm. In such a system, it is useful to apply the technology of Patent Document 1 to compensate the mass and inertia force of the master arm. Further, the present inventors have arrived at performing a friction compensation of the motor which drives each joint of the master arm.

Thus, a remote control robot system according to one aspect of the present disclosure includes a master arm configured to receive manipulation of an operator, and a slave arm having a plurality of control modes of an automatic mode in which the slave arm operates based on a prestored task program and a manual mode in which the slave arm operates based on the manipulation of the operator received by the master arm. The master arm includes one or more motors configured to drive joints of the master arm, and a motor actuator configured to generate a torque instruction value that operates the joints according to an external force applied to the master arm and give drive current corresponding to the torque instruction value to the motor. The motor actuator generates, when the control mode is the manual mode, the torque instruction value so that the joints operate according to the external force while resisting a frictional force of the motor.

In the remote control robot system described above, when the control mode is the manual mode, the motor actuator may calculate a friction compensation torque correcting value so that the joints operate according to the external force while resisting the frictional force of the motor, and generate the torque instruction value that is corrected by the friction compensation torque correcting value.

In the remote control robot system described above, since, when the control mode of the slave arm is the manual mode, the torque instruction value is generated so that the joints operate according to the external force while resisting the frictional force of the motor, the master arm operates so that a frictional resistance which the operator feels is reduced. Therefore, a manipulating force required for the manipulation of the master arm is reduced.

Effect of the Disclosure

According to the remote control robot system of the present disclosure, the manipulating force required for the manipulation of the master arm is reduced.

MODE FOR CARRYING OUT THE DISCLOSURE

Hereinafter, one embodiment of the present disclosure is described with reference to the drawings.

[Remote-Control Robot System 100]

Figure 1:
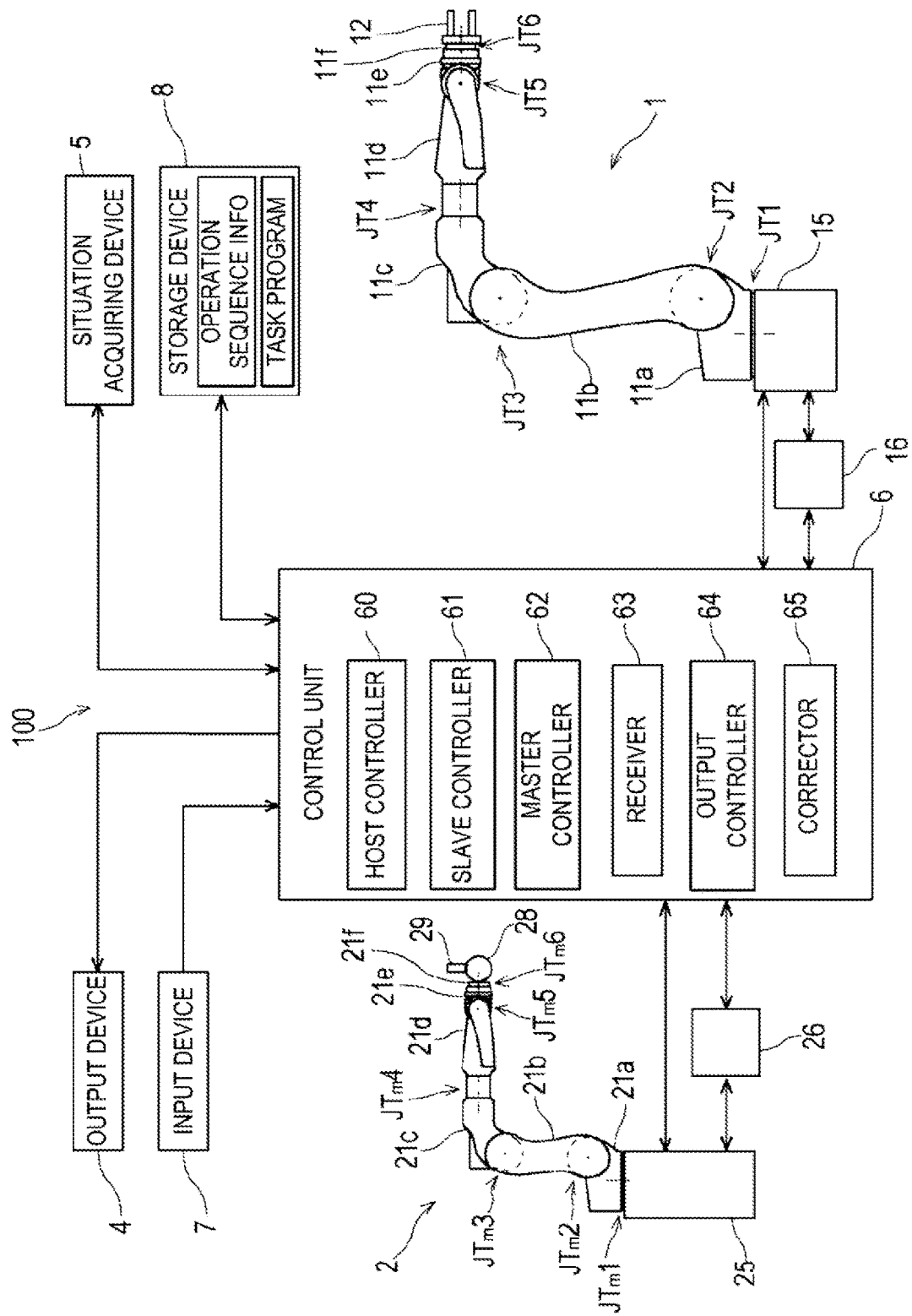
FIG. 1 is a block diagram illustrating an outline configuration of a remote control robot system according to one embodiment of the present disclosure.

FIG. 1 is a block diagram illustrating an outline configuration of a remote control robot system 100. As illustrated in FIG. 1, the remote control robot system 100 is a master-slave type robot system, and includes a slave arm 1, a master arm 2, an input device 7, an output device 4, a situation acquiring device 5, and a control unit 6 which comprehensively controls the system 100.

The slave arm 1 according to this embodiment has three control modes of an automatic mode, a manual mode, and a correctable automatic mode. The control mode of the slave arm 1 is switchable so that the operation is controlled by one selected from the plurality of control modes.

A control mode in which the slave arm 1 is operated according to a preset task program is herein referred to as the "automatic mode." In the automatic mode, the slave arm 1 automatically performs a given work without the manipulation of the master arm 2 by an operator, similar to a conventional teaching playback robot.

Moreover, the control mode in which the slave arm 1 is operated based on the manipulation of the operator received by the master arm 2 is herein referred to as the "manual mode." The master arm 2 is capable of receiving the manipulation inputted by the operator directly moving the master arm 2. Note that, in the manual mode, the manipulation of the operator received by the master arm 2, and the motion of the slave arm 1 which is operating based on the manipulation may be corrected automatically.

Moreover, the control mode in which the slave arm 1 is operated according to the preset task program while being sequentially corrected by the manipulation of the operator received by the master arm 2 is herein referred to as the "correctable automatic mode." In the correctable automatic mode, the motion of the slave arm 1 which is operating according to the preset task program is corrected based on the manipulation of the operator received by the master arm 2.

Below, each component of the remote control robot system 100 is described in detail.

[Slave Arm 1]

The slave arm 1 is an articulated robot arm having a plurality of joints JT1-JT6, which is comprised of a serially coupled body of a plurality of links 11a-11f, and a pedestal 15 which supports the coupled body. In more detail, at the first joint JT1, the pedestal 15 and a base-end part of the first link 11a are coupled to each other so as to be rotatable about an axis extending vertically. At the second joint JT2, a tip-end part of the first link 11a and a base-end part of the second link 11b are coupled to each other so as to be rotatable about an axis extending horizontally. At the third joint JT3, a tip-end part of the second link 11b and a base-end part of the third link 11c are coupled to each other so as to be rotatable about an axis extending horizontally. At the fourth joint JT4, a tip-end part of the third link 11c and a base-end part of the fourth link 11d are coupled to each other so as to be rotatable about an axis extending in the longitudinal directions of the fourth link 11d. At the fifth joint JT5, a tip-end part of the fourth link 11d and a base-end part of the fifth link 11e are coupled to each other so as to be rotatable about an axis perpendicular to the longitudinal directions of the fourth link 11d. At the sixth joint JT6, a tip-end part of the fifth link 11e and a base-end part of the sixth link 11f are twistably and rotatably coupled to each other. A mechanical interface is provided to a tip-end part of the sixth link 11f. An end effector 12 corresponding to the contents of work is attached to the mechanical interface attachably and detachably.

Figure 2:
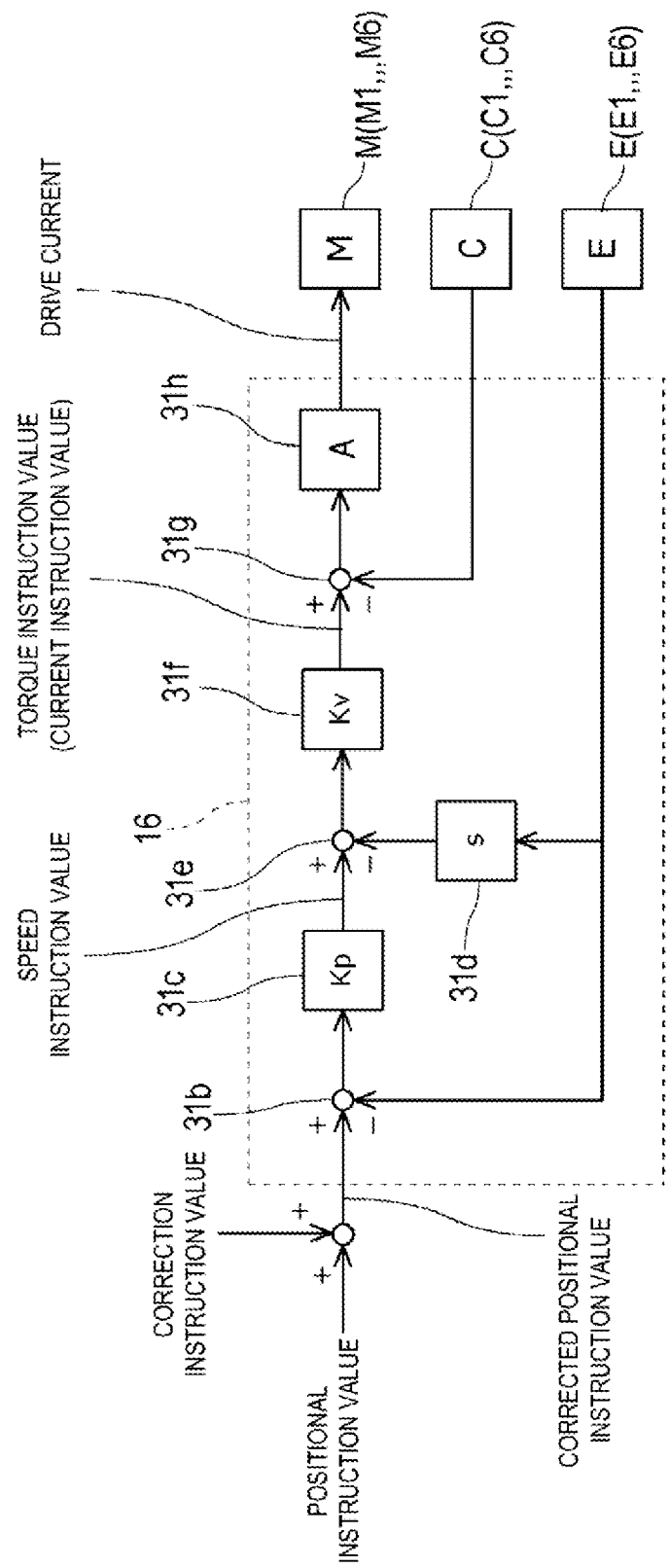
FIG. 2 is a block diagram illustrating a configuration of a control system of a slave arm.

FIG. 2 is a block diagram illustrating a configuration of a control system of the slave arm 1. In this figure, a concrete electric configuration focusing on a motor controller 16 is illustrated. As illustrated in FIG. 2, the joints JT1-JT6 of the slave arm 1 are provided with drive motors M1-M6, respectively, each of which relatively rotates two members connected by the joint, as one example of an actuator. Since a control system is provided to each of the drive motors M1-M6 and they have similar configuration, one of the control systems is representatively described.

The drive motors M1-M6 are, for example, servo motors which are servo-controlled by the motor controller 16. Moreover, the drive motors M1-M6 are provided with position sensors E1-E6 which detect rotational positions thereof and current sensors C1-C6 which detect current for controlling the rotations, respectively. The position sensors E1-E6 may be, for example, any sensors which are capable of detecting the rotational positions, such as encoders, resolvers, or pulse generators. Note that, in the description of the drive motors M1-M6, the position sensors E1-E6, and the current sensors C1-C6, 1-6 of the suffixes are given to the alphabet corresponding to the joints JT1-JT6, respectively. Below, when an arbitrary joint is illustrated among the joints JT1-JT6, the suffix is omitted and it is referred to as "JT," and the same is applied to the drive motor M, the position sensor E, and the current sensor C.

The drive motor M, the position sensor E, and the current sensor C are electrically connected with the motor controller 16. Although the motor controller 16 according to this embodiment is capable of servo-controlling the plurality of drive motors M alone, motor controllers may be provided corresponding to the respective drive motors M.

The motor controller 16 generates a torque instruction value (current instruction value) based on a positional instruction value, a servo gain, etc. which are acquired from the control unit 6 (in detail, a slave controller 61) described later, and supplies drive current corresponding to the torque instruction value to the drive motor M. The output rotational angle of the drive motor M is detected by the position sensor E, and is fed back to the motor controller 16. Note that the functions of the motor controller 16 and the slave controller 61 may be implemented as a single circuit or a single arithmetic device.

When the positional instruction value is inputted into the motor controller 16 from the control unit 6 (in detail, the slave controller 61), the inputted positional instruction value is given to the plus-side input of a subtractor 31b. A signal indicative of the rotational angle (present position value) detected by the position sensor E is given to the minus-side input of the subtractor 31b. In the subtractor 31b, the rotational angle is subtracted from the positional instruction value. The output of the subtractor 31b is given to a coefficient multiplier 31c, where the output is amplified by a position gain Kp, and is then given to the + input of a subtractor 31e. The resultant obtained by a differentiator 31d differentiating the rotational angle from the position sensor E is given to the − input of the subtractor 31e. The output of the subtractor 31e is given to a coefficient multiplier 31f, where the output is amplified by a speed gain Kv, and is given to the + input of a subtractor 31g. The current value from the current sensor C is given to the − input of the subtractor 31g. The subtracted output of the subtractor 31g is inputted into an amplifier circuit 31h as the torque instruction value, and the amplified torque instruction value and corresponding drive current are supplied to the drive motor M.

[Master Arm 2]

The master arm 2 is a means to receive the manipulation of the operator. In the remote control robot system 100 according to this embodiment, the slave arm 1 operates so that a hand part of the slave arm 1 moves to follow the motion of the hand part of the master arm 2. That is, the master arm 2 is configured to be able to instinctively manipulate the position and posture of the slave arm 1. In detail, the position and posture of the hand part of the master arm 2 (or changes of the position and posture) are received as the manipulation of the operator, and the control unit 6 generates the positional instruction value corresponding to the manipulation of the operator so that the hand part of the slave arm 1 moves to follow the motion of the hand part of the master arm 2.

The master arm 2 is an articulated robot arm having a plurality of joints JTm1-JTm6, the number of which is the same as the slave arm 1. The master arm 2 is comprised of a pedestal 25 and a plurality of links 21a-21f, which are serially coupled. The serially-coupled configuration of the links 21a-21f of the master arm 2 is substantially the same as the links 11a-11f of the slave arm 1 and, thus, detailed description thereof is omitted. A gripper 29 is attached to the tip-end part of the sixth link 21f of the master arm 2 (i.e., the hand part of the master arm 2) through a 6-axis force sensor 28. The configuration of a drive system of the master arm 2 will be described in detail later.

[Input Device 7]

The input device 7 is an input means, which is installed outside a workspace together with the master arm 2, receives an operational instruction from the operator and inputs the received operational instruction into the control unit 6. Into the input device 7, operations other than the manipulation according to the position and posture of the slave arm 1 are inputted. The input device 7 is provided with one or more operational input tools which input the operation instructions other than the position and posture of the slave arm 1, such as an operational input tool for selecting the control mode of the slave arm 1 and an emergency stop switch. The one or more operational input tools may include known operational input tools, such as a touch panel, a key, a lever, a button, a switch, and a dial plate, for example. Moreover, a mobile terminal, such as a programmable display device (pendant) or a tablet computer, may be used as the input device 7.

[Situation Acquiring Device 5]

The situation acquiring device 5 is a means for acquiring situation information indicative of a situation of the slave arm 1 in the workspace. The situation information includes information used in order to recognize the position, the posture and the like of the slave arm 1 in the workspace, or a situation around the slave arm 1. More specifically, the situation information includes information required for enabling the recognition of the situation of the slave arm 1 and the situation around the slave arm 1 in the workspace, such as the position and posture of the slave arm 1 in the workspace, a spatial relationship between the slave arm 1 and a workpiece, a spatial relationship between the slave arm 1 and an assembled component to which an assembling component is attached, or the like, for example.

The situation acquiring device 5 is implementable by, for example, a sensor, a camera device, a communication device, an encoder, etc. The sensor may be, for example, a laser sensor, a radar sensor or the like for measuring the distance or the position to the assembling component or the assembled component. Further, it may also be a stereoscopic camera which is a sensor for measuring the distance from the slave arm 1 to an object around the slave arm 1 by using image data obtained from a plurality of imaging devices. The communication device may be a communication device, for example, which acquires information from the assembling component or the assembled component, or a sensor and an imaging device installed at given positions in the workspace. The encoder may be, for example, an encoder capable of detecting an amount of movement or the position of the slave arm 1.

The situation acquiring device 5 acquires the situation information sequentially, and the acquired situation information is inputted into the control unit 6 described later, where it is used for the motion control of the slave arm 1. Further, the control unit 6 may also be configured to control the output device 4 to output the situation information. The situation acquiring device 5 may be attached to the slave arm 1, or may be attached to a suitable position in the workspace. Moreover, the attached number of situation acquiring devices 5 may be one, or may be plural. The attached positions and the attached number are arbitrary, as long as the suitable number of situation acquiring devices 5 are attached at positions where the situation information are appropriately acquirable.

[Output Device 4]

The output device 4 is to output the information transmitted from the control unit 6. The output device 4 is installed at a position where it is easy to be visually recognizable by the operator who is operating the master arm 2. The output device 4 includes at least a display device, and may further include a printer, a speaker, a hazard light, etc. The display device displays and outputs the information transmitted from the control unit 6. For example, the speaker outputs the information transmitted from the control unit 6 as sound. Moreover, for example, the printer prints out and outputs the information transmitted from the control unit 6 on recording media, such as paper.

[Storage Device 8]

The storage device 8 stores various task programs used for the control of the slave arm 1. The task program may be created as an operation flow for each work. The task program is created, for example, by teaching, and is stored in the storage device 8 so as to be associated with identifying information on the slave arm 1 and a task. Note that, although the storage device 8 is described independently from the control unit 6, a storage device provided to the control unit 6 may function as the storage device 8.

Moreover, the storage device 8 stores operation sequence information created beforehand. The operation sequence information is information related to an operation sequence which defines a series of work processes to be carried out by the slave arm 1 in the workspace. In this operation sequence information, an operation order of the work processes is associated with the control mode of the slave arm 1. Moreover, in this operation sequence information, each work process is associated with the task program for causing the slave arm 1 to automatically perform the work. Note that the operation sequence information may include, for each work process, the program for causing the slave arm 1 to automatically perform the work.

[Control Unit 6]

As illustrated in FIG. 1, the control unit 6 is communicatably connected with the slave arm 1, the master arm 2, the output device 4, the situation acquiring device 5, the input device 7, and the storage device 8 wiredly or wirelessly.

The control unit 6 is a so-called computer, and has an arithmetic processing part, such as a CPU, and a memory part, such as a ROM and/or a RAM (none of them is illustrated). The memory part stores a control program executed by the control unit 6, various fixed data, etc. The arithmetic processing part performs, for example, transmission and reception of data with external devices, such as the input device 7, the output device 4, and the storage device 8. Moreover, the arithmetic processing part inputs the detection signals from the various sensors and outputs the control signal to each controlled target. In the control unit 6, the arithmetic processing part reads and executes software, such as the program stored in the memory part, to perform processing for controlling various operations of the system 100. Note that, the control unit 6 may execute each processing by a centralized control with a single computer, or may execute each processing by a distributed control with a collaboration of a plurality of computers. Moreover, the control unit 6 may be comprised of a microcontroller, a programmable logic controller (PLC), etc.

The control unit 6 includes, as functional blocks, a host controller 60, the slave controller 61, a master controller 62, a receiver 63, an output controller 64, and a corrector 65. Although these functional blocks are collectively illustrated in the single control unit 6 in FIG. 1, each functional block or a combination of a plurality of functional blocks may be implemented by one or more independent computers. In this case, part of these functional blocks may be disposed in the workspace, and the rest may be disposed outside the workspace.

The slave controller 61 controls the operation of the slave arm 1. When in the automatic mode, the slave controller 61 reads the task program stored in the storage device 8, generates the positional instruction value according to the task program, and gives the positional instruction value, the servo gain, etc. to the motor controller 16 of the slave arm 1. Moreover, when in the manual mode, the slave controller 61 generates the positional instruction value based on the manipulating information which is accepted by the master arm 2 and received by the receiver 63, and gives the positional instruction value, the servo gain, etc. to the motor controller 16 of the slave arm 1. Moreover, when in the correctable automatic mode, the slave controller 61 reads the task program stored in the storage device 8, generates the positional instruction value (or a corrected positional instruction value) based on the task program and a correction instruction value acquired from the corrector 65, and gives the positional instruction value, the servo gain, etc. to the motor controller 16 (see FIG. 2). Note that, if the correction instruction value is not given from the corrector 65 in the correctable automatic mode, the correction instruction value may be calculated as zero.

The master controller 62 controls the motion of the master arm 2. The master controller 62 operates the master arm 2 so that the master arm 2 moves or changes in the posture according to an external force which the operator gives to the master arm 2. That is, the manipulating force of the operator is assisted by the motion of the master arm 2. Alternatively, when the operator gives the external force to the master arm 2, the master controller 62 may operate the master arm 2 so that the hand part of the master arm 2 moves along a given route.

The receiver 63 receives an input signal transmitted from the outside of the control unit 6. The input signal received by the receiver 63 may be, for example, the signal transmitted from the master arm 2, the signal transmitted from the input device 7, the signal indicative of the situation information transmitted from the situation acquiring device 5, etc.

The output controller 64 controls the output device 4 to output to the output device 4 information to be notified to the operator. For example, the output device 4 outputs to the display device, the information for identifying the target slave arm 1, and information for urging the input of the selection of the control mode of the slave arm 1, when starting a selected portion of the operation sequence. Moreover, for example, the output device 4 outputs to the display device the situation information and the operating situation of the slave arm 1 manipulated by the master arm 2, when the control mode of the slave arm 1 is the manual mode and the correctable automatic mode. Moreover, for example, the output device 4 outputs an alarm to the speaker or the display device, when a malfunction occurs to the system 100.

The corrector 65 corrects the motion of the slave arm 1 based on the manipulation received by the master arm 2, when the control mode of the slave arm 1 is in the correctable automatic mode. For example, when the position and posture of the master arm 2 are changed by the operator moving the master arm 2, the master arm 2 receives displacements of the position and posture as a correction instruction, and inputs it into the control unit 6. While the control mode of the slave arm 1 is in the correctable automatic mode, when the receiver 63 receives a correction instruction signal, the corrector 65 generates a correction instruction value based on the correction instruction signal. Equation(s) or map(s) to obtain the correction instruction value from the correction instruction signal are stored beforehand Such a correction instruction value may be, for example, a value proportional to amounts of change in the position and posture of the master arm 2. The generated correction instruction value is transmitted to the slave controller 61, and a corrected positional instruction value is outputted from the slave controller 61 to the motor controller 16 (see FIG. 2).

The host controller 60 reads the operation sequence information stored in the storage device 8, and outputs instructions to the slave controller 61, the master controller 62, the output controller 64, and the corrector 65 so that the slave arm 1, the master arm 2, the output device 4, and the situation acquiring device 5 operate in accordance with the operation sequence information.

[Operation of Remote-Control Robot System 100]

Next, one example of the operation of the remote control robot system 100 of the above configuration is described. Here, an operation flow of the system 100 is described, while the remote control robot system 100 is established as an automobile assembly line, and it is applied to a case where the slave arm 1 performs a work to attach a seat to an automobile. Note that the remote control robot system 100 according to the present disclosure is not limited to such an automobile assembly line, but may be applied widely to various production facilities.

The operation sequence information on the seat attaching work to an automobile body stored in the storage device 8 is comprised of a component extracting task T1 in which the seat is extracted from a container, a component carrying task T2 in which the seat is carried to near an attaching position of the body, and a component attaching task T3 in which the seat located near the attaching position is attached to the attaching position, and these tasks T1-T3 are repeatedly performed in this order. Among this operation sequence, the component extracting task T1 and the component carrying task T2 are "automatic portions" in which the slave arm 1 operates in the automatic mode. The automatic portion of the operation sequence is associated with the automatic mode as the control mode. Moreover, the component attaching task T3 of the operation sequence is the "selected portion" in which the slave arm 1 operates in the control mode selected from the automatic mode, the manual mode, and the correctable automatic mode. The selected portion of the operation sequence is not associated with a specific control mode, but the control mode is selectable therein.

First, the control unit 6 reads given operation sequence information stored in the storage device 8, and starts the control of the system 100 in accordance with the operation sequence information.

In accordance with the case of the operation sequence of the seat attaching work to the automobile body described above, the control unit 6 first reads the task program of the component extracting task T1 from the storage device 8 and executes it. Next, the control unit 6 reads the task program of the component carrying task T2 and executes it. In the component extracting task T1 and the component carrying task T2, the control unit 6 controls the operation of the slave arm 1 in the automatic mode.

Once the component carrying task T2 is finished, the control unit 6 displays the selection screen for demanding selection of the control mode of the following component attaching task T3 from an operator on the display device. Besides, the control unit 6 causes the display device to output the situation information on the slave arm 1 in which the control mode is about to be selected. Here, the situation information which is displayed and outputted to the display device may include the identifying information on the slave arm 1 currently displayed, the contents of the process to be performed next, etc.

The operator visually recognizes the situation information on the slave arm 1 displayed on the display device, and selects one of the three control modes. The selection of the control mode by the operator is received by the master arm 2 or the input device 7, and is inputted into the control unit 6.

In the above, if the automatic mode is selected, the control unit 6 reads the task program of the component attaching task T3 from the storage device 8, and controls the operation of the slave arm 1 in the automatic mode. Moreover, if the manual mode is selected, the control unit 6 controls the operation of the slave arm 1 in the manual mode. Alternatively, if the correctable automatic mode is selected, the control unit 6 controls the operation of the slave arm 1 in the correctable automatic mode.

In the above, if one of the manual mode and the correctable automatic mode is selected, the control unit 6 displays and outputs the situation information on the slave arm 1 to the display device throughout the process. As described above, the control unit 6 sequentially advances the work process along the operation sequence.

[Configuration of Drive System of Master Arm 2]

Figure 3:
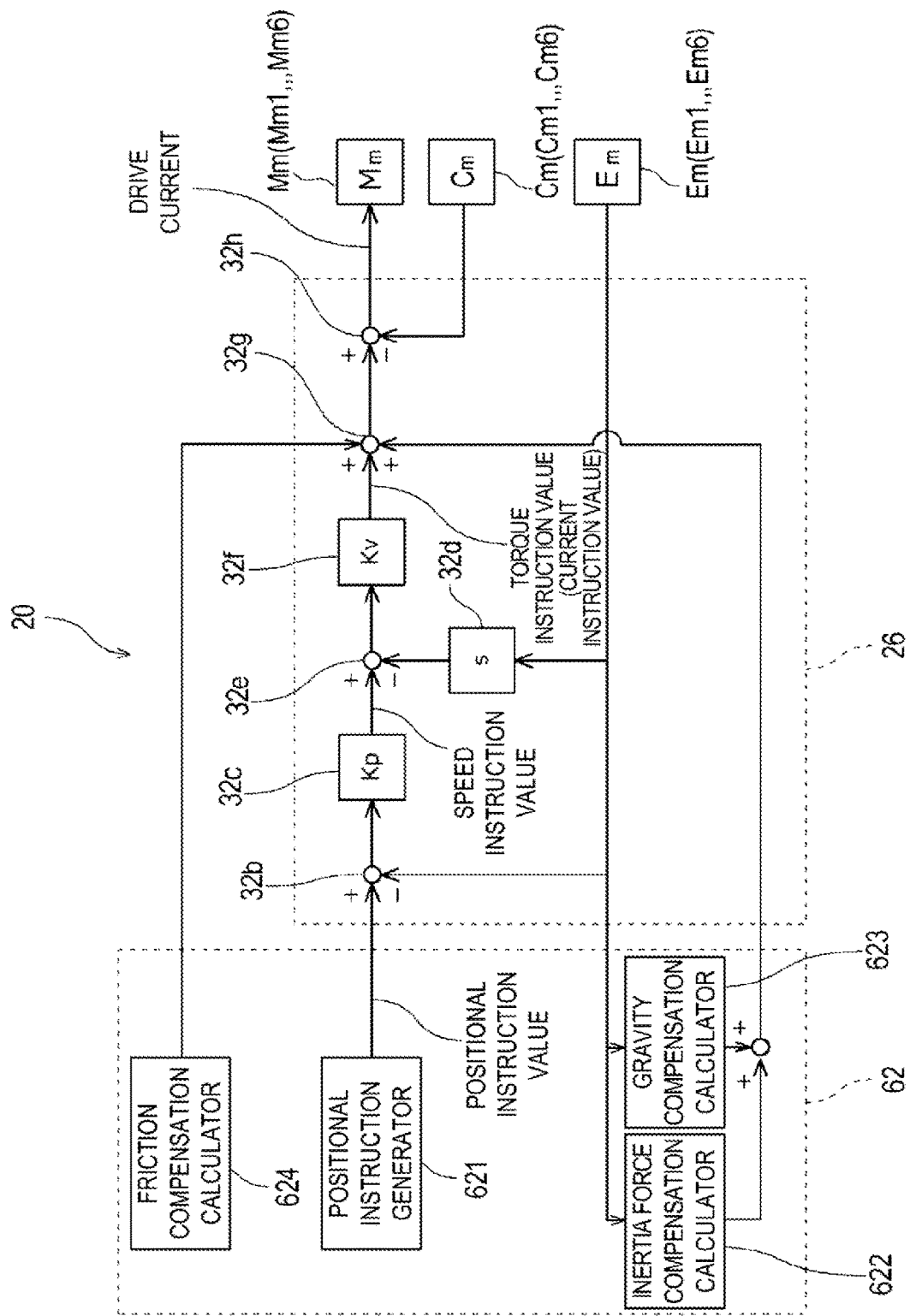
FIG. 3 is a block diagram illustrating a configuration of a motor actuator of the master arm.

Here, the configuration of the drive system of the master arm 2 is described in detail. FIG. 3 is a block diagram illustrating a configuration of a motor actuator 20 of the master arm 2.

As illustrated in FIG. 3, joints JTm1-JTm6 of the master arm 2 are provided with drive motors Mm1-Mm6, respectively, each of which relatively rotates two members connected by the joint, as one example of an actuator. Since the motor actuator 20 is provided to each of the drive motors Mm1-Mm6 and they have similar configuration, one of the motor actuators 20 is representatively descried.

The drive motors Mm1-Mm6 are, for example, servo motors which are servo-controlled by the motor controller 26. Moreover, the drive motors Mm1-Mm6 are provided with position sensors Em1-Em6 which detect rotational positions thereof and current sensors Cm1-Cm6 which detect current for controlling the rotations, respectively. The position sensors Em1-Em6 may be, for example, any sensors which are capable of detecting rotational positions, such as encoders, resolvers, or pulse generators. Note that, in the description of the drive motors Mm1-Mm6, the position sensors Em1-Em6, and the current sensors Cm1-Cm6, 1-6 of the suffixes are given to the alphabet corresponding to the joints JTm1-JTm6, respectively. Below, when an arbitrary joint is illustrated among the joints JTm1-JTm6, the suffix is omitted and it is referred to as "JTm," and the same is applied to the drive motor Mm, the position sensor Em, and the current sensor Cm.

The drive motor Mm, the position sensor Em, and the current sensor Cm are electrically connected with the motor controller 26. Although the motor controller 26 according to this embodiment is capable of servo-controlling the plurality of drive motors Mm1-Mm6 alone, the motor controllers may be provided corresponding to the respective drive motors Mm.

The motor controller 26 generates a torque instruction value (current instruction value) based on a positional instruction value, a servo gain, etc. which are acquired from the control unit 6 (in detail, the master controller 62), and supplies drive current corresponding to the torque instruction value to the drive motor Mm. The output rotational angle of the drive motor Mm is detected by the position sensor Em, and is fed back to the motor controller 26. The master controller 62, the motor controller 26, the position sensor Em, the current sensor Cm, etc. constitute the motor actuator 20 of the master arm 2. Note that the functions of the motor controller 26 and the master controller 62 may be implemented as a single circuit or a single arithmetic device.

The master arm 2 according to this embodiment is provided with an assist mechanism which helps the operator's manipulating force by performing an inertia force compensation, a gravity compensation, and a friction compensation of the master arm 2. The assist mechanism is implemented by the drive motor Mm provided to each joint JTm of the master arm 2, a non-illustrated power-train mechanism (including a gear-reduction mechanism etc.) which transmits the output of the drive motor Mm to each joint JTm, and the motor actuator 20 which drives the drive motor Mm, etc.

Figure 4:
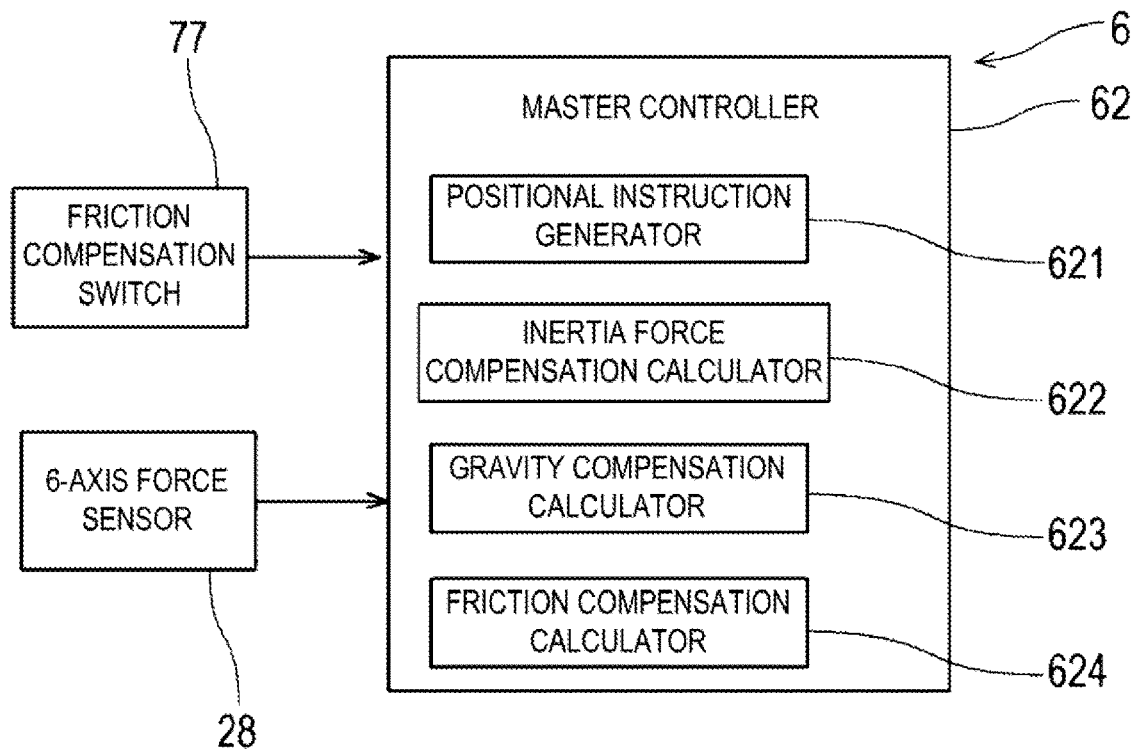
FIG. 4 is a functional block diagram of a master controller.

FIG. 4 is a functional block diagram of the master controller 62. The master controller 62 has functional parts of a positional instruction generator 621, an inertia force compensation calculator 622, a gravity compensation calculator 623, and a friction compensation calculator 624. A signal which switches ON/OFF of a friction compensation is given to the master controller 62 from a friction compensation switch 77 (friction compensation switching means) which switches ON/OFF of the friction compensation. The friction compensation switch 77 may be provided to the master arm 2, the gripper 29, or the input device 7. Moreover, sensor outputs are given to the master controller 62 from the 6-axis force sensor 28 and the position sensor Em. The 6-axis force sensor 28 outputs a signal according to an external force (torque) applied to the master arm 2 through the gripper 29 (i.e., the operator's manipulating force).

The positional instruction generator 621 calculates the position, posture, and driving speed of each joint JTm of the master arm 2 based on the sensor output of the position sensor Em, and calculates the magnitude and direction of the external force which the operator applied to the master arm 2 based on the sensor output of the 6-axis force sensor 28. Then, the positional instruction generator 621 generates positional instruction values based on these calculation values, and outputs them to the motor controller 26.

The inertia force compensation calculator 622 generates an inertia force compensation torque correcting value for compensating the inertia force acting on the master arm 2 based on the sensor output of the position sensor Em. An angular velocity is obtained by differentiating the rotational angle which is the sensor output of the position sensor Em, an angular acceleration is obtained by differentiating the angular velocity, and an inertia force compensation torque correcting value can be generated using the angular acceleration.

Moreover, the gravity compensation calculator 623 generates a gravity compensation torque correcting value for compensating the gravity acting on the master arm 2 based on the sensor output of the position sensor Em. The gravity compensation torque correcting value is calculated by preset formula(s). The inertia force compensation torque correcting value and the gravity compensation torque correcting value are combined, and it is given to the motor controller 26 as an inertia-force/gravity compensation torque correcting value. Note that the inertia force compensation torque correcting value and the gravity compensation torque correcting value may be given to the motor controller 26 as independent signals. Moreover, here, although the inertia force compensation torque correcting value and the gravity compensation torque correcting value are calculated independently, the inertia-force/gravity compensation torque correcting value which combines the inertia force compensation torque correcting value and the gravity compensation torque correcting value may be calculated by calculation. Note that the gravity compensation calculator 623 can be omitted from the control system of the drive motor Mm for driving the joint of which the motion is not influenced by gravity.

Figure 5:
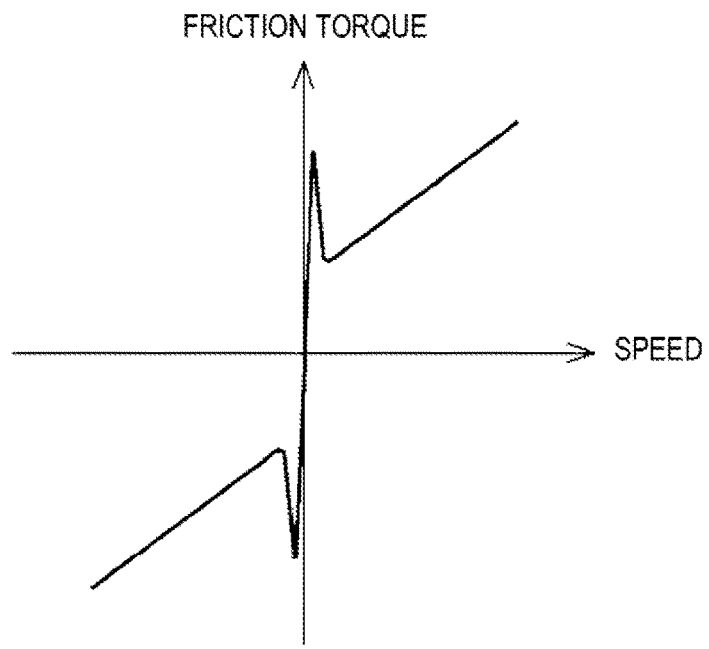
FIG. 5 is one example of a friction model.

The friction compensation calculator 624 generates a friction compensation torque correcting value for compensating the frictional force produced at each joint JTm of the master arm 2. FIG. 5 illustrates one example of a friction model of the drive motor Mm. In the friction model illustrated in FIG. 5, both static friction and kinetic friction are considered, where the static friction acts in a direction opposite from the input when stopped, and Coulomb's friction acts in a direction opposite from movement when moving (i.e., when the speed is not 0). The control unit 6 stores the friction model of each drive motor Mm beforehand. Note that, below, although the frictional force produced at the drive motor Mm is compensated using the friction model of the drive motor Mm, a frictional force produced at the joint Jm may be compensated using a friction model of the drive motor Mm and the power-train mechanism which transmits the output to the joint Jm.

The friction compensation torque correcting value is generated based on the prestored friction model, and the sensor outputs of the 6-axis force sensor 28 and the position sensor Em, as such a value that the static friction is reduced when stopped or the kinetic friction is reduced when moving. The friction compensation torque correcting value may be such a value that the operator is able to move the master arm 2 without feeling any resistance. The generated friction compensation torque correcting value is given to the motor controller 26.

Returning to FIG. 3, when the positional instruction value generated in the master controller 62 is inputted into the motor controller 26 as described above, the inputted positional instruction value is given to the plus-side input of a subtractor 32*b*. A signal indicative of the rotational angle detected by the position sensor Em (present position value) is given to the minus-side input of the subtractor 32*b*. The subtractor 32*b* subtracts the rotational angle from the positional instruction value. The output of the subtractor 32*b* is given to a coefficient multiplier 32*c*, where it is amplified by the position gain Kp, and is then given to the + input of a subtractor 32*e*. The resultant obtained by a differentiator 32*d* differentiating the rotational angle from the position sensor Em is given to the − input of the subtractor 32*e*. The output of the subtractor 32*e* is given to a coefficient multiplier 32*f*, where it is amplified by the speed gain Kv, and is then given to the + input of an adder 32*g*. The friction compensation torque correcting value and the inertia-force/gravity compensation torque correcting value are given to another + inputs of the adder 32*g*. Thus, the torque instruction value corrected by the friction compensation torque correcting value, the inertia force compensation torque correcting value, and the gravity compensation torque correcting value is given to the + input of the subtractor 32*h*. The current value from the current sensor Cm is given to − input of the subtractor 32. The subtracted output of the subtractor 32*h* is inputted into an amplifier circuit (not illustrated) as a corrected torque instruction value, and drive current corresponding to the amplified torque instruction value is supplied to the drive motor Mm.

Note that the motor actuator 20 switches ON/OFF of the friction compensation according to the control mode of the slave arm 1 and the operation of the friction compensation switch 77. Specifically, since the master arm 2 is not manipulated when the slave arm 1 is in the automatic mode, all of the inertia force compensation, the gravity compensation, and the friction compensation of the master arm 2 may be OFF. When the inertia force compensation, the gravity compensation, and the friction compensation are OFF, the inertia force compensation torque correcting value, the gravity compensation torque correcting value, and the friction compensation torque correcting value may not be generated, or the supply of these compensation values to the motor controller 26 may be intercepted, or these compensation values may be zero.

When the slave arm 1 is in the manual mode, the inertia force compensation and the gravity compensation are ON, and, in principle, the friction compensation is OFF. When the friction compensation is OFF, the friction compensation torque correcting value may not be generated, the supply of the friction compensation torque correcting value to the motor controller 26 may be intercepted, or the friction compensation torque correcting value may be zero regardless of the frictional force.

Note that, even if the slave arm 1 is in the manual mode, the friction compensation may also be ON in addition to the inertia force compensation and the gravity compensation when the friction compensation switch 77 is ON. For example, if the operator turns on the friction compensation switch 77 when beginning to move the master arm 2, he/she is able to move the master arm 2 with a lightweight manipulating force from the beginning of the manipulation.

When the slave arm 1 is in the correctable automatic mode, all of the inertia force compensation, the gravity compensation, and the friction compensation are ON. Although the manipulation received by the master arm 2 is reflected on the motion of the slave arm 1 when in the correctable automatic mode, the manipulation of the master arm 2 may be assumed to be little in amount, like when correcting a minute deviation of the route. Thus, by performing the friction compensation of the master arm 2, a dead zone where the manipulation inputted into the master arm 2 is processed as a disturbance becomes smaller, and even if the amount of manipulation is little, the master arm 2 is capable of receiving it as the manipulating input.

As described above, the remote control robot system 100 according to this embodiment includes the master arm 2 which receives the manipulation of the operator, and the slave arm 1 having the plurality of control modes of the automatic mode in which it operates based on the prestored task program, the manual mode in which it operates based on the manipulation of the operator received by the master arm 2, and the correctable automatic mode in which it operates based on the task program while being corrected sequentially by the manipulation of the operator received by the master arm 2. The master arm 2 has one or more drive motors Mm which drive the joint(s) of the master arm 2, and the motor actuator 20 which generates the torque instruction value for operating the joint JTm according to the external force applied to the master arm 2 and gives the drive current corresponding to the torque instruction value to the motor (s). When the control mode is the correctable automatic mode, the motor actuator 20 generates the torque instruction value so that the joint JTm operates according to the external force, while resisting the frictional force of the drive motor Mm.

In the embodiment described above, when the control mode is the correctable automatic mode, the motor actuator 20 calculates the friction compensation torque correcting value for the joint JTm operating according to the external force while resisting the frictional force of the drive motor Mm, and generates the torque instruction value which is corrected by the friction compensation torque correcting value.

Note that, in the embodiment described above, the motor actuator 20 calculates the friction compensation torque correcting value based on the prestored frictional-force model of the drive motor Mm. Note that the calculating method of the friction compensation torque correcting value is not limited to the above configuration, but it may be obtained by an equation, a map, etc.

In the remote control robot system 100 described above, by generating the torque instruction value so that the joint JTm operates according to the external force while resisting to the frictional force of the drive motor Mm, the master arm 2 operates so that the frictional resistance which the operator feels is reduced. Particularly in the correctable automatic mode among the plurality of control modes of the slave arm 1, it is assumed that the operator intermittently moves the master arm 2 and manipulates it abruptly and, thus, it is demanded that the master arm 2 can be lightly manipulated in such a situation. Therefore, if the master arm 2 operates so that the frictional resistance which the operator feels is reduced when the slave arm 1 is in the correctable automatic mode, the demand is satisfied. Thus, in the remote control robot system 100 described above, the friction compensation according to the control mode of the slave arm 1, i.e., the use mode of the master arm 2, can be performed.

Note that the master arm 2 which operates as described above is implementable by making a change in software with the same hardware of a general-purpose industrial robot arm. That is, the general-purpose industrial robot arm which can be applied to the slave arm and other industrial robots can be used as the master arm 2, without using a robot arm dedicated for the master arm. For example, when establishing the remote control robot system 100, labors and cost to manufacture the master arm 2 for exclusive use are eliminated by using the general-purpose industrial robot arm as the hardware of the master arm 2. Moreover, for example, when the remote control robot system 100 is dismissed, the hardware of the master arm 2 can be reused as the general-purpose industrial robot arm. Note that, when adopting the general-purpose industrial robot arm as the master arm 2, a detachable cushion covering may be attached to the master arm 2 in order to ease an impact at the time of contact of the master arm 2 and the operator.

Moreover, in the embodiment described above, the master arm 2 further has the friction compensation switch 77 (switching means) which switches ON/OFF of the friction compensation, and the motor actuator 20 generates the torque instruction value which is corrected by the friction compensation torque correcting value, when the control mode is the manual mode and the friction compensation switch 77 is ON.

According to this, when the slave arm 1 is in the manual mode, the friction compensation occurs if the friction compensation switch 77 is ON, and the operator is able to move the master arm 2 lightly, without feeling any friction. When the friction compensation switch 77 is OFF, the friction occurs at the joint JTm and, thus, the master arm 2 is prevented from being operated by the disturbance.

Moreover, in the embodiment described above, the motor actuator 20 generates the inertia force compensation torque correcting value which compensates the inertia force acting on the master arm 2, and generates the torque instruction value which is corrected by the inertia force compensation torque correcting value. Further, in the embodiment described above, the motor actuator 20 generates the gravity compensation torque correcting value which compensates the gravity acting on the master arm 2, and generates the torque instruction value which is corrected by the gravity compensation torque correcting value.

Thus, in the remote control robot system 100 according to the embodiment, the inertia force and the gravity acting on the master arm 2 are also compensated and, thus, the operator is able to move the master arm 2, without feeling the mass and inertia of the master arm 2.

Although the suitable embodiment of the present disclosure is described above, the above configuration may be changed as follows, for example.

In the embodiment described above, although the slave arm 1 and the master arm 2 are both the 6-axis vertical articulated robot arms, the slave arm 1 and the master arm 2 may be horizontal articulated robot arms, and the number of joints (i.e., the number of axes) is not limited, either.

Moreover, in the embodiment described above, although the master controller 62 is described as part of the control unit 6, the master controller 62 may be configured as a control device which is independent from other components of the control unit 6.

Moreover, in the master arm 2 according to the embodiment described above, the friction compensation is carried out when the slave arm 1 is in the correctable automatic mode, but ON/OFF of the friction compensation may be switched by the friction compensation switch 77 also in the correctable automatic mode, similar to the manual mode. In this case, the motor actuator 20 generates the torque instruction value which is corrected by the friction compensation torque correcting value, when the control mode of the slave arm 1 is in the correctable automatic mode and the friction compensation switch 77 is ON. In other words, the motor actuator 20 does not perform the friction compensation, when the control mode of the slave arm 1 is in the correctable automatic mode and the friction compensation switch 77 is OFF and, thus, the master arm 2 is prevented from being operated by the disturbance.

Moreover, although the master arm 2 according to the embodiment described above carries out the friction compensation when the slave arm 1 is in the manual mode and the friction compensation is ON at the friction compensation switch 77, the friction compensation may be carried out only with a condition that the slave arm 1 is in the manual mode, regardless of ON/OFF of the friction compensation switch 77. In this case, the motor actuator 20 generates the torque instruction value which is corrected by the friction compensation torque correcting value, when the control mode is the manual mode. Therefore, for example, it becomes possible to move the master arm 2 even if the amount of manipulation is very small.

Moreover, in the remote control robot system 100 according to the embodiment described above, although the slave arm 1 has the plurality of control modes of the automatic mode, the manual mode, and the correctable automatic mode, the slave arm 1 may have a plurality of control modes of the automatic mode and the manual mode. In this case, the friction compensation of the master arm 2 is carried out, when the slave arm 1 is in the manual mode, similar to the embodiment described above.

The suitable embodiment of the present disclosure is described above. It is apparent for a person skilled in the art that many improvements and other embodiments of the present disclosure are possible from the above description. Therefore, the above description is to be interpreted only as illustration, and it is provided in order to teach a person skilled in the art the best mode which implements the present disclosure. Details of the structures and/or the functions may substantially be changed, without departing from the spirit of the present disclosure.

DESCRIPTION OF REFERENCE CHARACTERS

1: Slave Arm
2: Master Arm
4: Output Device
5: Situation Acquiring Device
6: Control Unit
7: Input Device
8: Storage Device
11a-11f: Link
12: End Effector
15: Pedestal
16: Motor Controller
20: Motor Actuator
21a-21f: Link
25: Pedestal
26: Motor Controller
28: 6-Axis Force Sensor
29: Gripper
60: Host Controller
61: Slave Controller (Slave Control Device)
62: Master Controller (Master Control Device)
63: Receiver
64: Output Controller
65: Corrector
77: Friction Compensation Switch
100: Remote-control Robot System
621: Positional Instruction Generator
622: Inertia Force Compensation Calculator
623: Gravity Compensation Calculator
624: Friction Compensation Calculator
C, C1-C6, Cm, Cm1-Cm6: Current Sensor
E, E1-E6, Em, Em1-Em6: Position Sensor
JT, JT1-JT6, JTm, JTm1-JTm6: Joint
M, M1-M6, Mm, Mm1-Mm6: Drive Motor

What is claimed is:
1. A remote control robot system, comprising:
hardware constituted by a general-purpose industrial robot arm including a plurality of links consecutively connected to each other through joints, one or more motors configured to drive the joints, and a motor actuator configured to apply drive current to the one or more motors;
a processor programed to operate the general-purpose industrial robot arm such that the general-purpose industrial robot arm serves as a master arm configured to receive manipulation of an operator; and
a slave arm having a plurality of control modes including an automatic mode in which the slave arm operates based on a prestored task program and a manual mode in which the slave arm operates based on the manipulation of the operator received by the master arm,
wherein, in the manual mode, the motor actuator (i) generates a torque instruction value that operates the joints according to an external force applied to the master arm, (ii) calculates a friction compensation torque correcting value so that the joints operate according to the external force while resisting a frictional force of the one or more motors, and (iii) generates the torque instruction value that is corrected by the friction compensation torque correcting value.

2. The remote control robot system of claim 1, wherein, the master arm further includes a switching means configured to switch ON/OFF of the friction compensation, and
the motor actuator generates, in the manual mode, the torque instruction value that is corrected by the friction compensation torque correcting value in response to the switching means being ON.

3. The remote control robot system of claim 1, wherein, the plurality of control modes further includes a correctable automatic mode in which the slave arm operates based on the task program, while being corrected sequentially, by the manipulation of the operator received by the master arm, and
in the correctable automatic mode, the motor actuator calculates the friction compensation torque correcting value so that the joints operate according to the external force while resisting the frictional force of the one or more motors, and generates the torque instruction value that is corrected by the friction compensation torque correcting value.

4. The remote control robot system of claim 3, wherein, the master arm further includes a switching means configured to switch ON/OFF of the friction compensation, and
the motor actuator generates, in the correctable automatic mode, the torque instruction value that is corrected by the friction compensation torque correcting value in response to the switching means being ON.

5. The remote control robot system of claim 1, wherein the motor actuator generates an inertia force compensation torque correcting value that compensates an inertia force acting on the master arm, and generates the torque instruction value that is corrected by the inertia force compensation torque correcting value.

6. The remote control robot system of claim 1, wherein the motor actuator generates a gravity compensation torque correcting value that compensates gravity acting on the master arm, and generates the torque instruction value that is corrected by the gravity compensation torque correcting value.

7. The remote control robot system of claim 1, wherein the motor actuator calculates the friction compensation torque correcting value based on a prestored frictional-force model of the one or more motors.

* * * * *